United States Patent [19]
Raatz et al.

[11] Patent Number: 5,157,198
[45] Date of Patent: Oct. 20, 1992

[54] PROCESS FOR ISOMERIZING NORMAL PARAFFINS IN THE PRESENCE OF AT LEAST ONE CATALYST BASED ON A PARTICULAR OMEGA ZEOLITE

[75] Inventors: Francis Raatz, Saint Avold; Christine Travers, Rueil Malmaison; Christian Marcilly, Houilles; Thierry Descourieres, Lyons; Francois Fajula, Teyran; Francois Figueras, Montpellier, all of France

[73] Assignees: Institut Francais Du Petrole, Rueil-Malmaison; Elf France, La Defense, both of France

[21] Appl. No.: 785,192

[22] Filed: Nov. 1, 1991

Related U.S. Application Data

[63] Continuation-in-part of Ser. No. 649,867, Feb. 4, 1991, abandoned.

[30] Foreign Application Priority Data

Feb. 2, 1990 [FR] France .................................. 90 01320

[51] Int. Cl.$^5$ ................................................ C07C 5/13
[52] U.S. Cl. .................................... 585/739; 585/750; 585/751
[58] Field of Search .................... 585/739, 750, 751

[56] References Cited

U.S. PATENT DOCUMENTS

| | | | |
|---|---|---|---|
| 4,665,272 | 5/1987 | Bakas et al. | 585/751 |
| 4,665,273 | 5/1987 | Johnson et al. | 585/751 |
| 4,827,076 | 5/1989 | Kokayeff et al. | 585/739 |
| 4,886,935 | 12/1989 | Kokayeff et al. | 585/739 |

Primary Examiner—Patrick P. Garvin
Assistant Examiner—E. D. Irzinski
Attorney, Agent, or Firm—Millen, White & Zelano

[57] ABSTRACT

The invention relates to a process for isomerizing normal paraffins, particularly $C_5$–$C_6$, in the presence of at least one catalyst based on an omega zeolite having a molar ratio $SiO_2/Al_2O_3$ ranging from 6.5 to 80, a content by weight of sodium lower than 0.2%, crystalline parameters "a" and "c" respectively smaller than or equal to 1.814 nm and 0.760 nm, a capacity of adsorption of nitrogen, measured at 77K under a partial pressure of 0.19, higher than about 8% by weight, the catalyst also comprising at least one metal from group VIII of the periodic table of elements, preferably platinum or/and palladium.

15 Claims, No Drawings

PROCESS FOR ISOMERIZING NORMAL PARAFFINS IN THE PRESENCE OF AT LEAST ONE CATALYST BASED ON A PARTICULAR OMEGA ZEOLITE

This application is a continuation-in-part of application Ser. No. 07/649,867, filed Feb. 4, 1991, now abandoned.

BACKGROUND OF THE INVENTION

The present invention relates to a process for isomerizing (or hydroisomerizing) normal paraffins, particularly normal paraffins having 4, 5, 6 or 7 atoms of carbon per molecule, in the presence of at least one catalyst based on a particular omega zeolite (or mazzite).

The isomerization of normal paraffins, notably with a low molecular weight, is of considerable importance in the oil industry, in view of the particularly high octane number of isoparaffins.

It is therefore interesting to be able to convert $C_4$–$C_7$ and especially, $C_5$–$C_6$-n-paraffins into isoparaffins in order to obtain a fuel with a high octane number. This process allows improving light gasoline fractions and particularly straight-run head fractions.

There are mainly three different types of processes for the isomerization of normal paraffins:

"low temperature" processes (about 20° to 130° C.), utilizing a catalyst of the Friedel-Crafts type, such as aluminum chloride, "average temperature" processes (about 150° C.), utilizing as a catalyst a supported metal such as platinum on halogenated alumina, and "high temperature" processes (at least 250° C.), utilizing zeolitic supports generally associated with a hydrogenating metal from group VIII of the periodic table of elements.

The thermodynamic equilibrium is more favorable to isoparaffins at low temperature, one advantage of the first two types of processes. These processes nevertheless have major drawbacks: catalysts of the Friedel-Crafts type and platinum on halogenated alumina catalysts, because of their corrosive nature, require very costly reactors made of special alloys and they are, moreover, very sensitive to water and to traces of sulfur.

"High temperature" processes have been the subject of numerous patents for about twenty years. Most catalysts that are described therein are made of zeolite, generally mordenite, in the acid form, with or without a hydrogenation promoter.

Mordenite-based catalysts obtained with the following treatments have thus been claimed:

exchange of $Na^+$ ions by $NH_4^+$ or $H^+$ ions (U.S. Pat. No. 3,190,939), acid treatment:

hot acid—$NH_4^+$ succession (U.S. Pat. No. 3,442,794)

hot acid—cold acid succession (U.S. Pat. No. 3,475,345)

acid solution containing $Na^+$ or $K^+$ ions U.S. Pat. Nos. 2,272,737, 4,359,409 and 4,400,576), thermal treatments under controlled humidity (U.S. Pat. Nos. 2,181,928, 3,836,597, and 3,842,114).

In the same vein, other patents relate to processes for dealuminizing mordenite:

severe acid treatments: HCl 12N, 100° C. (U.S. Pat. No. 3,480,539), self-steaming (calcining in a cured atmosphere) between 430° and 820° C., followed by acid attack (U.S. Pat. No. 3,506,400 and 3,551,353).

The use, for the isomerization of normal paraffins, of a mordenite with a particular morphology, modified by a succession of thermal treatments and acid treatments, is also described in U.S. Pat. No. 4,727,217.

DETAILED DESCRIPTION OF THE INVENTION

It has been discovered in the present invention that it is particularly advantageous to use, for the isomerization of normal paraffins and notably for $C_5$–$C_6$ normal paraffins, at least one catalyst based on a properly modified omega zeolite (or mazzite), a catalyst which shows improved performance in relation to the mordenite-based catalysts in prior art.

The omega zeolite (or mazzite) used in the present invention has a molar ratio $SiO_2/Al_2O_3$ ranging from 6.5 to 80, preferably from 10 to 40, a content by weight of sodium lower than 0.2%, preferably lower than 0.1%, in relation to the weight of dry zeolite. It usually has crystalline parameters "a" and "c" respectively smaller than or equal to 1.814 nm and 0.760 nm (1 nm = $10^{-9}$ m), preferably respectively ranging from 1.814 to 1.794 nm and from 0.760 to 0.749 nm, a capacity of adsorption of nitrogen, measured at 77K under a partial pressure of 0.19, higher than about 8% by weight, preferably higher than about 11% by weight. Its pore distribution generally comprises 5 to 50% of the pore volume contained in pores with a radius (measured with the BJH method) ranging from 1.5 to 14 nm, preferably from 2.0 to 8.0 nm (mesopores). In a general way, its crystallinity rate DX (measured from its X-ray diffractogram) is higher than 60%.

The omega zeolite used in the present invention is advantageously prepared from an omega zeolite obtained by synthesis (called an "original" omega zeolite), having a molar ratio $SiO_2/Al_2O_3$ ranging from 6 to 10, a content by weight of sodium generally ranging from 4 to 6.5% in relation to the weight of dry zeolite, a pore volume determined by nitrogen adsorption (at 77K under a partial pressure of 0.19) ranging from 0.05 to 0.15 $cm^3/g^{-1}$ and a surface area of 550 $m^2/g$, more preferably 500 $m^2/g$ or less, i.e., 450 or 450 $m^2g$; the crystalline structure of the original omega zeolite consists of series of $SiO_4$ and $AlO_4$ tetrahedrons generating big channels with dodecagonal openings parallel to the axis $\bar{c}$. The original omega zeolite may or may not contain a significant amount of organic cations according to whether it has been synthetized in the presence or in the absence of organic cations.

In order to obtain the omega zeolite (dealuminized, stabilized and impoverished in sodium ions) used in the present invention, the original omega zeolite is preferably subjected to the following well-known treatments:

Removal of the organic cations, particularly the tetramethylammonium ions that may be present at the time of its synthesis, through a calcination, under a mixture of inert gas (nitrogen for example) plus air in a molar ratio inert gas/air usually ranging from 3:1 to 7:1, then generally under pure air, at a temperature usually ranging from 450° to 650° C., preferably from 520° to 600° C., for a duration generally ranging from 0.5 to 6 hours, preferably from 1 to 4.5 hours.

Removal of the sodium cations through at least one cationic exchange where the sodium cations are replaced by ammonium cations, at a temperature generally ranging from 10° to 150° C., in a solution of at least one ionizable ammonium salt (generally ammonium nitrate), with a molarity usually ranging from 0.5 to 20N, preferably from 4 to 12N. The obtained product can then be optionally subjected to at least one washing with demineralized water at room temperature (10° to 30° C.).

Calcination in the presence of steam, the calcination atmosphere containing at least 1% and preferably at least 5% of steam, at a temperature generally ranging from 300° to 800° C., preferably from 400° to 700° C., the duration of this thermal treatment usually ranging from 0.2 to 8 hours, preferably from 1 to 6 hours.

Acid attack(s) in a solution of at least one strong mineral or organic acid, generally HCl or $HNO_3$, with a normality ranging from 0.05 to 6N, preferably from 0.1 to 4N, at a temperature usually ranging from 20° to 150° C., preferably from 80° to 150° C., for a duration generally greater than 0.2 hour, preferably greater than 1 hour.

It is possible to reverse order of the removal of the organic cations and the sodium cations, or else to omit the stage of thermal decomposition of the organic cations in case the latter are not present in notable amounts.

It is also possible to carry out one or several calcinations in the presence of steam—acid attack(s) sequences.

The catalyst, based on an omega zeolite modified thereby, used in the present invention, also usually comprises a generally amorphous matrix selected for example from the group consisting of clays, aluminas, silica, magnesia, zircon, titanium oxide, boron oxide and any combination of at least two of the compounds cited above, such as silica-alumina, silica-magnesia, alumina-boron oxide. The omega zeolite+matrix mixture is shaped by any method known by the man skilled in the art, such as, for example, extrusion, pelletizing, bowl granulation, oil drop, . . . The content by weight of omega zeolite in the obtained support (omega zeolite+-matrix) usually ranges from 30 to 98%, preferably from 60 to 90%.

Said catalyst generally comprises, apart from the omega zeolite (and possibly a matrix), at least one metal from group VIII of the periodic table of elements, preferably selected from the group consisting of platinum, palladium and nickel. Platinum and palladium are the most preferred metals.

The hydrogenizing metal from group VIII, preferably platinum and/or palladium, is deposited on the support by any process known by one skilled in the art. The technique of cationic exchange with competition can be notably used, where the competing agent is preferably ammonium nitrate. In the case of platinum or palladium, a platinum tetramine complex or a palladium tetramine complex is usually utilized; these metals will then deposit almost totally on the omega zeolite. This technique of cationic exchange can also be used for directly depositing the metal on the zeolite powder, before its optional mixing with a matrix.

It is also possible to deposit the platinum or the palladium no longer directly on the omega zeolite but on the alumina (if alumina is the matrix that is used), before or after the shaping stage, by carrying out an anionic exchange with hexachloroplatinic acid, hexachloropalladic acid and/or palladium chloride in the presence of a competing agent, for example hydrochloric acid.

The deposition of the metal (or metals) is generally followed by calcination under air or oxygen usually between 300° and 600° C. for 0.5 to 10 hours, preferably between 350° and 550° C. for 1 to 4 hours. A reduction under hydrogen, for example between 350° and 550° C. for 1 to 4 hours, can then be optionally achieved.

The content by weight of metal from group VIII in the catalyst usually ranges, in the case of platinum and palladium, from 0.05 to 1%, preferably from 0.1 to 0.6%, and, in the case of nickel, from 0.1 to 10%, preferably from 0.2 to 5%.

According to the process of the invention, the feedstock containing normal paraffins, preferably light normal paraffins with 5 or 6 atoms of carbon, and hydrogen are contacted with at least one catalyst described above, under the isomerization conditions mentioned below. This contacting may notably be performed by using said catalyst in fixed bed(s), in fluidized bed(s) or in batch (that is to say discontinuously).

The process according to the invention is usually implemented between 200° and 300° C., and preferably between 210° and 280° C., at pressures ranging from 0.1 to 7 MPa, and preferably from 0.5 to 5 MPa. The space velocity can range from 0.1 to 10, preferably from 0.15 to 5 liters of liquid hydrocarbons per liter of catalyst and per hour. The molar ratio $H_2$/feedstock generally ranges from 0.5 to 30, and preferably from 1 to 25. The isomerization being a balanced reaction, the isomerizate generally still contains a rather large amount of non converted normal paraffins. These paraffins can be separated from the isomers for example by distillation or by fractionating on a molecular sieve and recycled in the isomerization unit used for performing the process according to the invention.

EXAMPLES

The following examples illustrate the invention without however limiting the scope thereof.

EXAMPLE 1

Preparation of a catalyst A in accordance with that which is used in the invention.

The raw material that is used is an omega zeolite synthetized in the (Na, TMA) system according to the method described in French patent application 2,582,234. This omega zeolite shows, after the synthesis, a molar ratio $SiO_2/Al_2O_3$ of 6.4, a content by weight of sodium of 5.7% in relation to the weight of dry zeolite, a pore volume determined by adsorption of nitrogen (at 77K under a partial pressure of 0.19) of 0.062 $cm^3.g^{-1}$, crystalline parameters "a" and "c" respectively equal to 1.822 and 0.764 nm (1 nm = $10^{-9}$ m).

This original omega zeolite is subjected to a calcination at about 550° C., first under a nitrogen+air mixture at the rate of 2 $l.h^{-1}$.(g of zeolite)$^{-1}$ of nitrogen and 0.4 $l.h^{-1}$.(g of zeolite)$^{-1}$ of air for 2 hours, then in the same conditions under pure air. The product obtained thereby undergoes then 4 successive cationic exchanges in a solution of ammonium nitrate 4N, at a temperature of 100° C., for about 4 hours, the volume (V) of solution used being equal to 4 times the weight (W) of dry zeolite (V/W=4 $cm^3/g$). It is then subjected to a calcination in the presence of steam, the calcination atmosphere containing 50% of steam, at a temperature of 650° C., for 4 hours. It undergoes then an acid attack in a solution of hydrochloric acid 0.8N the volume (V') of which equals 10 times the weight (W') of dry zeolite (V'/W' = 10 $cm^3/g$), at a temperature of 100° C., for about 4 hours.

The obtained omega zeolite has a molar ratio $SiO_2/Al_2O_3$ of 30.4, a content by weight of sodium lower than 0.06%, crystalline parameters "a" and "c" respectively equal to 1.807 nm and 0.755 nm, a capacity of adsorption of nitrogen measured at 77K under a partial pressure of 0.19 equal to 17.7% by weight and a crystallinity rate DX of 85%.

This omega zeolite is then mixed with alumina; the obtained mixture, containing 20% by weight of alumina, is forced through a die, then dried and calcined.

Platinum is then deposited on the support consisting of the omega zeolite and the alumina through a cationic exchange from tetramine platinum chloride $Pt(NH_3)_4Cl_2$, ammonium nitrate being the competing ion.

The content by weight of platinum in the catalyst A obtained thereby is 0.3%.

EXAMPLE 2

Preparation of a catalyst B in accordance with that which is used in the invention.

Catalyst B is different from catalyst A prepared in example 1 in that the acid attack is achieved with a solution of hydrochloric acid 0.15N.

The obtained omega zeolite has a molar ratio $SiO_2/Al_2O_3$ of 7.2, a content by weight of sodium of 660 ppm, crystalline parameters "a" and "c" respectively equal to 1.811 nm and 0.753 nm, a capacity of adsorption of nitrogen measured at 77K under a partial pressure of 0.19 equal to 12% by weight and a crystallinity rate DX of 89%.

The stages of zeolite-alumina mixing, of shaping and of deposition of platinum are identical to those described in example 1.

The content by weight of platinum in the catalyst B obtained thereby is 0.3%.

EXAMPLE 3

Preparation of a catalyst C in accordance with that which is used in the invention.

Catalyst C is different from the catalyst A prepared in example 1 in that the acid attack is achieved with a solution of hydrochloric acid 3N.

The obtained omega zeolite has a molar ratio $SiO_2/Al_2O_3$ of 44, a content by weight of sodium of 150 ppm, crystalline parameters "a" and "c" respectively equal to 1.800 nm and 0.753 nm, a capacity of adsorption of nitrogen measured at 77K under a partial pressure of 0.19 equal to 17.7% by weight and a crystallinity rate of 63%.

The stages of zeolite-alumina mixing, of shaping and of deposition of platinum are identical to those described in example 1.

The content by weight of platinum in the catalyst C obtained thereby is 0.3%.

EXAMPLE 4

Preparation of a catalyst D that is not in accordance with that which is used in the invention.

The raw material that is utilized is a "small pore" mordenite, reference Alite 150, manufactured by Société Chimique de la Grande Paroisse. Its chemical formula in the anhydrous state is: $NaAlO_2(SiO_2)_{5.5}$.

50 grams of this powder are dipped into a solution 2M of ammonium nitrate and the suspension is brought to 95° C. for two hours. The volume of the solution of nitrate ammonium used equals 4 times the weight of dry zeolite (V/W=4 cm$^3$/g). This operation of cationic exchange is repeated 3 times. After the 3rd exchange, the product is washed with water, at 20° C., for 20 minutes, with a ratio V/W equal to 4 cm$^3$/g. The sodium content, expressed in percent by weight in relation to the weight of dry solid, passes from 5.5 to 0.1%. The product is then filtered and subjected to a calcination in a faint atmosphere (self-steaming) at 600° C. for 2 hours (the calcination atmosphere containing at least 5% of steam). An acid attack is then achieved the solid is injected as a reflux into a solution of hydrochloric acid 0.6N at 90° C. for 2 hours, with a ratio V/W equal to 8 cm$^3$/g, where V is the volume of the solution of hydrochloric acid and W the weight of dry mordenite. The product is then filtered, washed with hydrochloric acid 0.1N and then with water.

The mordenite obtained thereby has a molar ratio $SiO_2/Al_2O_3$ of 24. Its content by weight of sodium is about 300 ppm. Its elementary mesh volume equals 2.75 nm$^3$.

The stages of mordenite-alumina mixing, of shaping and of deposition of platinum are identical to those described in example 1.

The content by weight of platinum in the catalyst D obtained thereby is 0.3%.

The preceding catalysts have surface areas as follows:

| catalyst | surface area (m2/g) | |
| --- | --- | --- |
| A | 489 | |
| B | 500 | |
| C | 400 | |
| D | 449 | mordenite (out of invention) |

EXAMPLE 5

Isomerization test.

The catalysts prepared in the previous examples are each tested in isomerization with a feedstock of normal hexane. To that effect, they are placed in a catalytic unit in a fixed bed and reduced under hydrogen at 450° C.

The operating conditions of the isomerization test are the following:
temperature: see table I
pressure: 2 MPa
space velocity in weight of feedstock per unit of weight of catalyst and per hour: 0.2
molar ratio H$_2$/feedstock: 20.

The performances of catalysts A, B, C and D, presented in table I, are defined by:

$$\text{n-hexane conversion (\%)} = \frac{\text{Mass of n-hexane in the feedstock} - \text{Mass of n-hexane in the end product}}{\text{Mass of n-hexane in the feedstock}} \times 100$$

$$\text{Isomerization selectivity (\%)} = \frac{\Sigma(\text{Mass of isomers in the end product})}{\Sigma(\text{Mass of products in the reaction})} \times 100$$

$$\text{Cracking selectivity (\%)} = \frac{\Sigma(\text{Mass of cracked products in the end product})}{\Sigma(\text{Mass of products in the reaction})} \times 100$$

$$\% \, 22DMC4 = \frac{\text{Mass of 22DMC4 in the end product}}{\Sigma(\text{Mass of isomers in the end product})} \times 100$$

(with 22DMC4 = 2,2-dimethyl butane).

TABLE I

|  | A | B | C | D |
|---|---|---|---|---|
| $SiO_2/Al_2O_3$ | 30.4 | 7.2 | 44 | 24 |
| n-hexane conversion (%) | 60 | 60 | 60 | 60 |
| Isomerization selectivity (%) | 98.3 | 99.3 | 99.5 | 98.3 |
| Cracking selectivity (%) | 1.7 | 0.7 | 0.5 | 1.7 |
| % 22DMC4 | 25 | 10 | 15 | 15 |
| Temperature (°C.) | 215 | 260 | 255 | 230 |

Reading Table I allows to establish a comparison, at isoconversion (60%), between, on the one hand, the results obtained with catalysts A, B and C and, on the other hand, the results obtained with catalyst D.

Catalyst A shows, in relation to catalyst D, a substantially increased activity (temperature lower by 15° C. to reach the same rate of conversion of the n-hexane) and a 22DMC4 selectivity, an isomer with a high octane number, that is markedly higher, while having the same isomerization selectivity.

Catalysts B and C, which are a little less active than catalyst D, show, even at higher temperatures, a higher isomerization selectivity and a strongly lower cracking selectivity (side reaction).

We claim:

1. A process for isomerizing normal paraffins under isomerization condition in the presence of hydrogen and at least one catalyst based on an omega zeolite having a molar ratio $SiO_2/Al_2O_3$ ranging from 6.5 to 80, a content by weight of sodium lower than 0.2%, crystalline parameters "a" and "c" respectively smaller than or equal to 1.814 nm and 0.760 nm, a capacity of adsorption of nitrogen, measured at 77K under a partial pressure of 0.19, higher than about 8% by weight, and a surface area of not more than 550 m²/g, said catalyst also comprising at least one metal from group VIII of the periodic table of elements.

2. A process according to claim 1 wherein said omega zeolite has a molar ratio $SiO_2/Al_2O_3$ ranging from 10 to 40 and a content by weight of sodium lower than 0.1%.

3. A process according to claim 1 wherein said omega zeolite has crystalline parameters "a" and "c" respectively ranging from 1.814 to 1.794 nm and from 0.760 to 0.749 nm and a capacity of adsorption of nitrogen, measured at 77K under a partial pressure of 0.19, higher than about 11% by weight.

4. A process according to claim 1 wherein said omega zeolite has a pore distribution comprising 5 to 50% of the pore volume being pores with a radius ranging from 1.5 to 14 nm.

5. A process according to claim 1 wherein said catalyst also comprises a matrix.

6. A process according to claim 5 wherein the content by weight of omega zeolite in the support comprising the omega zeolite and the matrix ranges from 30 to 98%.

7. A process according to claim 1 wherein said metal from group VIII is selected from the group consisting of platinum, palladium and nickel.

8. A process according to claim 7 wherein the content by weight of metal from group VIII in the catalyst ranges from 0.05 to 1% in the case where said metal is platinum or palladium and from 0.1 to 10% in the case where said metal is nickel.

9. A process according to claim 7 wherein said metal from group VIII is selected from the group consisting of platinum and palladium.

10. A process for isomerizing paraffins according to claim 1, wherein the paraffins are $C_{5-6}$-normal paraffins.

11. A process according to claim 1, wherein the catalyst has a surface area of 400 to 550 m²/g.

12. A process according to claim 1, wherein the catalyst has a surface area of 400 to 500 m²/g.

13. A process according to claim 1, wherein the catalyst has a surface area of 500 m²/g or less.

14. A process according to claim 1, wherein the catalyst has a surface area of 490 m²/g or less.

15. A process according to claim 1, wherein the catalyst has a surface area of 450 m²/g or less.

* * * * *